(12) United States Patent
Creekmore et al.

(10) Patent No.: US 10,028,953 B2
(45) Date of Patent: *Jul. 24, 2018

(54) PHARMACEUTICAL COMPOSITION OF ROSUVASTATIN CALCIUM

(71) Applicant: AstraZeneca UK Limited, London (GB)

(72) Inventors: Joseph Richard Creekmore, Wilmington, DE (US); Sanjeev Hukmichand Kothari, Wilmington, DE (US); Bradford J. Mueller, Wilmington, DE (US); Yingxu Peng, Wilmington, DE (US)

(73) Assignee: AstraZeneca UK Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/364,607

(22) Filed: Nov. 30, 2016

(65) Prior Publication Data

US 2017/0231988 A1   Aug. 17, 2017

Related U.S. Application Data

(63) Continuation of application No. 14/118,746, filed as application No. PCT/GB2012/051105 on May 17, 2012.

(60) Provisional application No. 61/577,165, filed on Dec. 19, 2011, provisional application No. 61/488,222, filed on May 20, 2011.

(51) Int. Cl.
| | | |
|---|---|---|
| *A61K 31/505* | (2006.01) | |
| *A61K 31/616* | (2006.01) | |
| *A61K 9/28* | (2006.01) | |
| *A61K 9/16* | (2006.01) | |
| *A61K 9/20* | (2006.01) | |
| *A61K 9/50* | (2006.01) | |
| *A61K 9/24* | (2006.01) | |
| *A61K 31/155* | (2006.01) | |
| *A61K 31/455* | (2006.01) | |

(52) U.S. Cl.
CPC ............ *A61K 31/505* (2013.01); *A61K 9/167* (2013.01); *A61K 9/1676* (2013.01); *A61K 9/1694* (2013.01); *A61K 9/209* (2013.01); *A61K 9/2086* (2013.01); *A61K 9/282* (2013.01); *A61K 9/2813* (2013.01); *A61K 9/2866* (2013.01); *A61K 9/2886* (2013.01); *A61K 9/2893* (2013.01); *A61K 9/501* (2013.01); *A61K 9/5015* (2013.01); *A61K 9/5042* (2013.01); *A61K 9/5073* (2013.01); *A61K 9/5078* (2013.01); *A61K 31/155* (2013.01); *A61K 31/455* (2013.01); *A61K 31/616* (2013.01)

(58) Field of Classification Search
None
See application file for complete search history.

(56) References Cited

U.S. PATENT DOCUMENTS

| 5,681,582 A | 10/1997 | Gilis et al. |
|---|---|---|
| 2005/0038077 A1 | 2/2005 | Kohlrausch |
| 2005/0096391 A1 | 5/2005 | Holm et al. |
| 2006/0149065 A1* | 7/2006 | Kumar .................. C07D 239/42 544/332 |
| 2009/0297599 A1 | 12/2009 | Viragh et al. |
| 2010/0239667 A1 | 9/2010 | Hemmingsen et al. |

FOREIGN PATENT DOCUMENTS

| CN | 101385731 A | 3/2009 |
|---|---|---|
| CN | 101574344 A | 11/2009 |
| DE | 102004038396 A1 | 3/2006 |
| EP | 0521471 A1 | 6/1992 |
| EP | 2233133 A1 | 9/2010 |
| KR | 2006/0091762 A | 8/2006 |
| KR | 2011/0097168 A | 8/2011 |
| WO | 1999/06035 A2 | 2/1999 |
| WO | 01/54668 A1 | 8/2001 |

(Continued)

OTHER PUBLICATIONS

International Search Report issued in corresponding International Patent Application No. PCT/GB2012/051105 dated Aug. 27, 2012.
Written Opinion issued in equivalent International Patent Application No. PCT/GB2012/051105 dated Aug. 27, 2012.
"Ergocalciferol," Hawley's Condensed Chemical Dictionary, 14th ed. (2002).

*Primary Examiner* — John Pak
*Assistant Examiner* — Daniel L Branson
(74) *Attorney, Agent, or Firm* — Morgan, Lewis & Bockius LLP

(57) ABSTRACT

The invention relates to pharmaceutical compositions containing rosuvastatin calcium of formula (I) and processes for their manufacture.

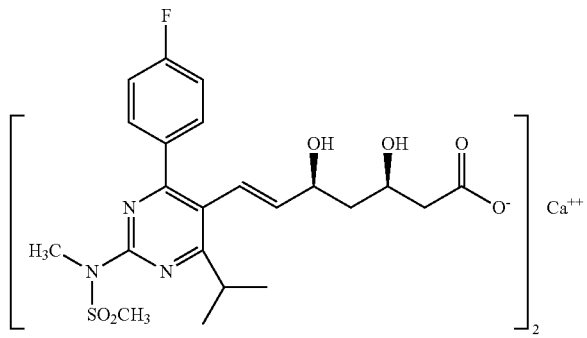

Formula I

1 Claim, 1 Drawing Sheet

(56) References Cited

FOREIGN PATENT DOCUMENTS

| | | |
|---|---|---|
| WO | 01/54669 A1 | 8/2001 |
| WO | 2005/084666 A1 | 9/2005 |
| WO | 2006/037348 A1 | 4/2006 |
| WO | 2006/071077 A1 | 7/2006 |
| WO | 2007/103557 A2 | 9/2007 |
| WO | 2008/023958 A1 | 2/2008 |
| WO | 2008/035128 A1 | 3/2008 |
| WO | 2008/054123 A1 | 5/2008 |
| WO | 2008/069546 A1 | 6/2008 |
| WO | 2008/124120 A1 | 10/2008 |
| WO | 2010/053343 A1 | 5/2010 |
| WO | 2010/066687 A2 | 6/2010 |
| WO | 2010/081824 A2 | 7/2010 |
| WO | 2011/081493 A2 | 7/2011 |

\* cited by examiner

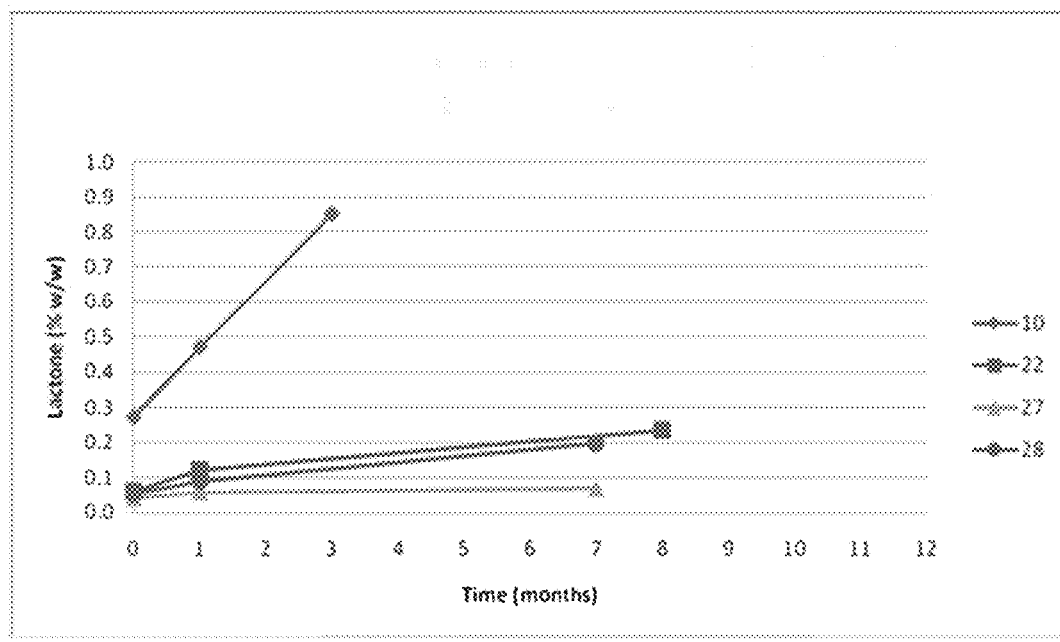

PHARMACEUTICAL COMPOSITION OF ROSUVASTATIN CALCIUM

The present invention relates to pharmaceutical compositions and more particularly to a pharmaceutical composition containing bis[(E)-7-[4-(4-fluorophenyl)-6-isopropyl-2-[methyl(methylsulfonyl)amino]pyrimidin-5-yl]-(3R,5S)-3,5-dihydroxyhept-6-enoic acid] calcium salt (of the formula I hereinafter, also known as rosuvastatin calcium and referred to hereinafter as "the Agent") and processes for their manufacture.

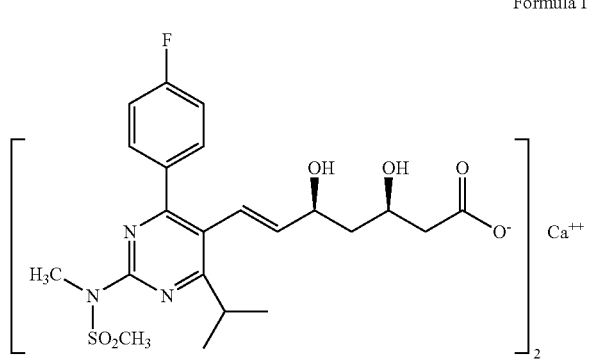

Formula I

The Agent is disclosed as an inhibitor of 3-hydroxy-3-methylglutaryl CoA reductase (HMG CoA reductase) in European Patent Application, Publication No. 0521471 and in Bioorganic and Medicinal Chemistry, (1997), 5(2), 437-444 and is useful in the treatment of hypercholesterolemia, hyperlipidproteinemia and atherosclerosis.

A problem associated with the Agent is that it undergoes degradation under certain conditions. This makes it difficult to formulate the product and provide a pharmaceutical composition with adequate storage life. The major degradation products formed are the corresponding (3R, 5S) lactone (hereinafter referred to as "the lactone") and an oxidation product (hereinafter referred to as "B2") in which the hydroxy group adjacent to the carbon-carbon double bond is oxidised to a ketone functionality.

It is therefore important to find a pharmaceutical composition of the Agent which remains stable over a prolonged period. It is also preferable that such a composition has a good flow rate to assist processing into unit dosage forms for oral administration, for example into tablets, and good disintegration and dissolution characteristics when processed into tablets for oral administration, which tablets can be in different dosage strengths. Our International Application WO01/54668 described such a stable tablet formulation.

Patients requiring statin therapy may also require simultaneous treatment for other cardiovascular conditions. A convenient alternative to taking multiple tablets is to provide a combination therapy of a statin with another commonly used cardiovascular medication in a single tablet. Formulating such a combination tablet may be problematic as, for example, the two active ingredients may need to be kept separate to avoid interaction with each other, or may need different conditions (such as pH or moisture content) in order for each of them to remain stable for the length of the tablet's shelf life. To give greatest flexibility in manufacture of a range of possible combination therapies, it would be advantageous to develop a process whereby the statin could be coated on to an inner core containing the other active ingredient, for example by spraying a solution containing the Agent onto an inner core such that evaporation of any solvent left a coat containing the Agent on the core (spray coating). However, in order to achieve robust and reproducible manufacture, the statin, such as the Agent, must be stable in the solution used in the coating process (coating solution) over a prolonged period. The instability of the Agent described above suggests that this would be very difficult to achieve.

WO2007/103557 describes a process for spray coating capsules with a coating containing an active ingredient and appears to be primarily directed towards solving the difficulties associated with spray coating capsules (size, smoothness and solubility of the capsule shell).

We have surprisingly found conditions under which the Agent may be spray coated on to a tablet core, which core may contain another active ingredient, and that the resulting tablet formulation would remain within acceptable limits for degradation products, including the lactone and B2 degradation products mentioned above, for the duration of a commercially viable shelf life, based on stability trials.

Analogously, the Agent may also be spray coated on to pellet or granule cores by the same process, and then these pellets or granules may be further formulated into, for example, tablets.

It will be understood therefore that reference to an "inner core" may be understood to refer to a tablet, pellet or granule core.

Therefore in a first aspect of the invention there is provided a pharmaceutical formulation comprising a rosuvastatin calcium containing layer spray coated onto a tablet, pellet or granule core, said rosuvastatin calcium containing layer comprising rosuvastatin calcium and a first coating polymer in a ratio of between approximately 1:8 to 2:1. In this context "approximately" is to be understood to mean+/−0.1.

In one aspect, the Agent is sprayed onto a tablet core. In another aspect, the Agent is sprayed onto a pellet core. In a further aspect, the Agent is sprayed onto a granule core.

When the Agent is sprayed onto a pellet or granule core, the coated core may be further processed by processes known in the art and/or described herein, to form a pharmaceutical product (such as a capsule or tablet).

In one embodiment, the first coating polymer comprises hypromellose (hydroxypropyl methylcellulose or HPMC) and polyethylene glycol (PEG). In another embodiment, the first coating polymer comprises polyvinyl alcohol (PVA) and polyethylene glycol (PEG).

Suitably the first coating polymer is provided as Opadry YS-1 10925A or Opadry 85F19250 or equivalents. Opadry YS-1 10925A contains 90.90% w/w hypromellose (hydroxypropyl methylcellulose) (type 2910, 6 cps) and 9.10% w/w polyethylene glycol 400 (and so is an HPMC/PEG mixture). Opadry 85F19250 contains 52.260% w/w polyvinyl alcohol part hydrolysed, 30.00% w/w talc, 14.74% w/w polyethylene glycol 3350 and 3.00% w/w polysorbate 80 (and so is a PVA/PEG mixture). Equivalent polymers will be understood to also have HPMC/PEG or PVA/PEG components in similar ratios to those in the two polymers described above. Additionally, HPC (hydroxypropyl cellulose) may be substituted for a portion of the HPMC. Also, alternative plasticizers such as triacetin, dibutyl sebecate, tributyl citrate, triethyl citrate, acetyltriethyl citrate, acetyltributyl citrate, dibutyl phthalate, diethyl phthalate, dimethyl phthalate, glycerine, propylene glycol, benzyl benzoate, 2-pyrrolidone, N-methylpyrrolidone, chlorobutanol, sorbitol, and/or diacetin may be used.

In one aspect, the rosuvastatin calcium containing layer further comprises a stabilisation agent, such as a compound to adjust the pH of the layer. In one embodiment the pH of the rosuvastatin calcium containing layer is between 5.6 and 11. In a further aspect, the pH is between 6 and 8. Examples of such stabilisation agents include sodium hydroxide and calcium acetate. It will be understood that a purpose of such pH adjustment is to help control rate of formation of degradation products.

In a further embodiment, a stabilisation agent may be added which is not directly intended to alter the pH. An example of such an agent is an antioxidant such as BHA (butylatedhydroxyanisol).

Further possible stabilisation agents include pharmaceutically acceptable hydroxides (such as sodium, potassium, calcium or aluminium hydroxides); pharmaceutically acceptable calcium salts of organic acids where the calcium replaces all the protons (such as calcium acetate, calcium lactate, calcium succinate and calcium fumarate) and their magnesium or aluminium equivalents; pharmaceutically acceptable inorganic magnesium silicates, magnesium aluminium silicates and aluminium silicates; pharmaceutically acceptable inorganic cationic salts containing calcium, potassium, sodium, aluminium, magnesium or lithium, in particular soluble salts.

Stabilisation agents which are any of the above salts of magnesium or calcium are particular embodiments of the invention.

BRIEF DESCRIPTION OF DRAWINGS

FIG. 1 illustrates the stability of Examples 3, 13, 18 and 19 (labelled as 10, 22, 27 and 28, respectively) by measurement of lactone formation over time at 25° C. at a relative humidity of 60% in HDPE bottles w/dessicant.

The moisture content of the tablet should be controlled and the rosuvastatin calcium containing layer dried sufficiently to achieve this. In one aspect the water content of the tablet is below 1.40% w/w. In a further aspect the water content is below 1.2% w/w, such as below 1.0% w/w, such as below 0.8% w/w. It will be understood that higher water contents tends to promote faster degradation of the rosuvastatin calcium. A higher water content may be tolerated in formulations containing other stabilisation agents, such as calcium acetate. In one aspect, formulations not containing a stabilisation agent as hereinbefore described, have a moisture content of below 0.8% w/w.

The water content was measured by weighing 10 tablets and heating the tablets at 50° C. at a relative humidity between 30 and 50% for 24 hours in an oven. The tablets were heated for approximately 24 h (not less than 23.5 h). After cooling to room temperature, the tablets were weighed again to calculate the moisture content.

It will be understood that, in order to measure the moisture content in each coat, then the above process must be carried after each coat is applied.

The rosuvastatin calcium containing layer is coated onto a tablet, pellet or granule core. In one aspect the tablet, pellet or granule core does not contain an active ingredient. In another aspect the tablet, pellet or granule core contains an active ingredient which is not rosuvastatin calcium. In a further aspect the tablet, pellet or granule core also contains rosuvastatin calcium. By "active ingredient" we mean an ingredient which has a desired biological activity.

In one aspect the tablet, pellet or granule core is coated with a sub-coating layer of a second coating polymer prior to spray coating with the rosuvastatin calcium containing layer. The second coating polymer may be any suitable polymer which is compatible with the first coating polymer used in the rosuvastatin containing layer. Advantageously the first and second coating polymers are the same. The presence of the sub-coating layer is essential if the tablet, pellet or granule core contains an active ingredient which is not compatible with rosuvastatin (for example because of its pH) as the sub-coating layer prevents contact between the two. The presence of the sub-coating layer is often desirable in order to provide a smooth surface for spraying the rosuvastatin containing layer onto, thus aiding uniformity of the rosuvastatin containing layer.

The second coating polymer in the sub-coating may be the same as the first coating to polymer in the rosuvastatin calcium containing layer, or may be different to but compatible with it. In one aspect, the first and second coating polymers are the same. Suitably the second coating polymer is provided as Opadry YS-1 10925A or Opadry 85F19250 or equivalents, as described hereinabove.

The tablet, pellet or granule core can be of any size suitable for coating using standard coating equipment. The tablet, pellet or granule core may be formulated for immediate release, controlled release or modified release, according to methods known in the art. It will be understood that herein the term "controlled release", which could also herein be described as "extended release" refers to formulations in which the active ingredient is released into the body over an extended period of time. It will be understood that herein the term "modified release" refers to formulations wherein the release of the active ingredient into the body occurs in a specified manner—for example, this could include release after a certain time delay or release under certain pH conditions (such as the use of an enteric coating to prevent release of the active ingredient until the tablet reaches a certain point in the digestive tract).

The tablet may also be formulated to disintegrate when chewed.

Optionally, the rosuvastatin calcium containing layer is coated with a top coat (outer coating) comprising a third coating polymer, for example to provide protection for the tablet against damage by impact, or the action of air, water or light. In one aspect the rosuvastatin calcium containing layer is coated with a top coat (outer coating). Suitably the top coat contains an HPMC-PEG or PVA-PEG (particularly a HPMC-PEG) polymer.

In one aspect the third coating polymer further comprises colouring agents and/or light opacifiers. Suitable colouring agents are any known in the art. Suitable light opacifiers are those known in the art, in particular titanium dioxide and/or ferric oxide.

In one aspect the third coating polymer further comprises ferric oxide (and optionally also titanium dioxide) in quantities sufficient to prevent light penetration of the top coat. It will be understood that there is greater potential for degradation due to the effect of light where the rosuvastatin calcium is spread in a thin layer all over the tablet core, rather than in a conventional tablet where the rosuvastatin is present as particles within a matrix of excipients. Hence a greater quantity of opacifier may be required to prevent degradation in the formulations of the present invention.

It has previously been found that ferric oxide is particularly effective at preventing light degradation of rosuvastatin (see WO01/54669). Therefore in a further aspect of the invention, the outer (top) coat comprises a light protective coating containing ferric oxide.

Suitably the third coating polymer top coat is provided as Opadry 03B94523 or Opadry II 85F94317. Opadry 03B94523 consists of 65.90% w/w hypromellose, type 2910, 6 cps, 9.10% w/w polyethylene glycol 400, 24.45% w/w titanium dioxide and 0.55% w/w red ferric oxide. Opadry II 85F94317 consists of 40.0% w/w polyvinyl alcohol part hydrolysed, 14.8% w/w talc, 20.2% w/w polyethylene glycol 3350, 24.27% w/w titanium dioxide and 0.73% w/w ferric oxide.

In one aspect, the third coating polymer is the same as the first coating polymer. In one embodiment the first, second and third coating polymers all comprise, for example, HPMC-PEG polymers. It will be understood that although the first, second and third coating polymers may all comprise an HPMC-PEG polymer, each layer may have differing additional components as described hereinbefore.

Additionally, other components may be added into the formulation for cosmetic or commercial purposes. For example a flavouring might be added in order to mask the taste of one or more component. Conveniently a flavouring may be added in the topcoat.

In an embodiment (IA) of the invention there is provided a pharmaceutical formulation comprising a rosuvastatin calcium containing layer coated onto a tablet, pellet or granule core, said rosuvastatin calcium containing layer comprising rosuvastatin calcium and an HPMC/PEG polymer in a ratio of between approximately 1:8 to 2:1, wherein the rosuvastatin calcium containing layer was coated onto the tablet, pellet or granule core by spray coating a solution of rosuvastatin calcium and an HPMC/PEG polymer in water.

In another embodiment (TB) of the invention there is provided a pharmaceutical formulation comprising a rosuvastatin calcium containing layer coated onto a tablet, pellet or granule core, said rosuvastatin calcium containing layer comprising rosuvastatin calcium and an HPMC/PEG polymer, wherein the formulation is further coated with an outer layer comprising an HMPC polymer and ferric oxide.

In another embodiment (IC) of the invention there is provided a pharmaceutical formulation comprising a tablet, pellet or granule core spray coated with a layer comprising rosuvastatin calcium in an HMPC/PEG polymer, wherein the formulation is further coated with an outer layer comprising an HMPC polymer and ferric oxide, wherein the rosuvastatin calcium containing layer was coated onto the tablet, pellet or granule core by spray coating a solution of rosuvastatin calcium and an HPMC/PEG polymer in water.

In one aspect of these embodiments (IA), (IB) and (IC), the tablet, pellet or granule core contains an active ingredient which is not rosuvastatin calcium. In a further aspect, this active ingredient is also not selected from any one or more of: niacin or a niacin analogue, a fibrate, metformin, a CETP inhibitor and/or aspirin. In a further aspect this active ingredient is useful for treating cardiovascular, thrombotic or diabetic diseases, although preferably is not one of the agents listed in the aspect within this paragraph above. In a further aspect, this active ingredient is selected from those listed hereinbelow.

In a further aspect of these embodiments (IA), (IB) and (IC), the solution comprising rosuvastatin calcium and an HPMC/PEG polymer further comprises a stabilisation agent, particularly calcium acetate or BHA, more particularly calcium acetate.

In a further aspect of these embodiments (IA), (IB) and (IC) the tablet, granule or pellet core is coated with a sub-coat of polymer (particularly an HPMC/PEG polymer) before spray coating with the solution of rosuvastatin calcium and an HPMC/PEG polymer in water.

It will be understood that a tablet core will contain various excipients as well as optionally an active ingredient (as herein described). Any conventional excipients may be used as known in the art (such as fillers, disintegrants or lubricants) provided they are compatible with any active ingredient present, and compatible with any coating polymer or with the rosuvastatin containing layer if they are in direct contact.

As mentioned hereinbefore, this method of formulating rosuvastatin may be applied to pellets or granules. It will be understood that such coated pellets or granules may themselves be formulated into tablets, and the third coating layer (outer coating or top coat) may then be applied to the overall tablet. In order to be further formulated, the coated pellets or granules may be mixed with other excipients and then compressed into tablets. It will be understood that this method would allow formation of, for example, chewable tablets, by processes known in the art.

Chewable tablets are designed to be chewed and not swallowed whole. Typically, a formulation for a chewable tablet will contain a sugar (e.g. sucrose) or sugar alcohol or polyol (such as mannitol or xylitol). The sugar alcohols may be preferred as they give a cooling sensation. Typically, chewable tablets contain a lubricant such as magnesium stearate, stearic acid, calcium stearate or a combination of these. Other lubricants include hydrogenated vegetable oil and sodium stearyl fumarate. Colour, flavouring and sweeteners may be added. Typical sweeteners are saccharin (or salts thereof), aspartame, acesulfame potassium, aspartame-acesulfame potassium combination, sucralose and stevia. A further possible sweetener is cyclamate (or salts thereof). Other ingredients such as starches (for example to increase the smoothness of the mouth feel) or glidants may be added if needed or desired.

After mixing, the tablets are compressed. Chewable tablets are typically larger than the usual tablets so that there is a sufficient volume to chew and/or increase the carrying capability of the tablet ingredients.

In order to incorporate the formulations of the invention, the chewable tablets would need to be formulated in the absence of water, for example by addition of the rosuvastatin containing granules after granulation is complete or as a direct compression mixture.

Orally disintegrating tablets (ODT) are designed to be placed on the tongue and disintegrate within a short period of time (such as in 30 seconds). While the mechanism of tablet breakage or disintegration is different from chewable tablets, there are a number of areas of commonality, such as the above discussion concerning the use of sugars, colours, sweeteners and flavourings. Advantageously, a flavouring which increases the production of saliva may be used, for example mint. Lubricants are used but the amount of lubricant must be limited because it will slow the water ingress or wicking.

Typically, the ODT contains a sugar alcohol or combination with other sugar alcohols and/or starch that are milled to a small particle size to facilitate rapid wicking and dissolution. The ingredients are mixed together as a powder blend. The amount of lubricant is limited and/or a tablet press that sprays lubricant onto the die wall is used.

As mentioned above, rosuvastatin calcium is an HMG-CoA reductase inhibitor and is well known for its effect on lowering Low Density Lipoprotein (LDL)-cholesterol. The pharmaceutical formulations of this invention are therefore useful for treating conditions associated with raised LDL-cholesterol. As the tablet, pellet or granule core may also contain an active ingredient, which may itself be useful against conditions other than those treated with HMG-CoA reductase inhibitors, the formulations of the invention may have a variety of possible uses.

Suitably the active ingredient which may be present in the tablet, pellet or granule core is selected from niacin and niacin analogues, biguanides (examples include metformin, phenformin, buformin), sulfonylureas (examples include chlorpropamide, glyburide, glimeperide), thiazolidinediones (examples include rosiglitazone, pioglitazone), DPP-4 inhibitors, SGLT-2 inhibitors, aldose reductase inhibitors, phosphodiesterase-5 inhibitors, amphipathic carboxylic acids (examples include fenofibrate, gemfibrizil), phosphodiesterase-3 inhibitor (examples include cilostazol), cholesterylester transfer protein (CETP) inhibitors, platelet aggregation inhibitors (examples include thienopyridines (example includes clopidigrel) prasugrel, aspirin), Factor Xa inhibitors, dipyridamole, peripheral calcium channel blockers, diuretics, angiotensin converting enzyme inhibitors, angiotensin II receptor antagonists, direct thombin inhibitors (examples include dabigatran), coenzyme Q-10, vitamin D1 (ergocalciferol) and vitamin D3 (cholecalciferol).

In a further aspect, suitably the active ingredient which may be present in the tablet, pellet or granule core is selected from biguanides (examples include metformin, phenformin, buformin), sulfonylureas (examples include chlorpropamide, glyburide, glimeperide), thiazolidinediones (examples include rosiglitazone, pioglitazone), DPP-4 inhibitors, SGLT-2 inhibitors, aldose reductase inhibitors, phosphodiesterase-5 inhibitors, phosphodiesterase-3 inhibitor (examples include cilostazol), platelet aggregation inhibitors (examples include thienopyridines (example includes clopidigrel) prasugrel), Factor Xa inhibitors, dipyridamole, peripheral calcium channel blockers, diuretics, angiotensin converting enzyme inhibitors, angiotensin II receptor antagonists, direct thombin inhibitors (examples include dabigatran), coenzyme Q-10, vitamin D1 (ergocalciferol) and vitamin D3 (cholecalciferol).

In a further aspect, suitably the active ingredient which may be present in the tablet, pellet or granule core is selected from sulfonylureas (examples include chlorpropamide, glyburide, glimeperide), thiazolidinediones (examples include rosiglitazone, pioglitazone), DPP-4 inhibitors, SGLT-2 inhibitors, aldose reductase inhibitors, phosphodiesterase-5 inhibitors, phosphodiesterase-3 inhibitor (examples include cilostazol), platelet aggregation inhibitors (examples include thienopyridines (example includes clopidigrel) prasugrel), Factor Xa inhibitors, dipyridamole, peripheral calcium channel blockers, diuretics, angiotensin converting enzyme inhibitors, angiotensin II receptor antagonists, direct thombin inhibitors (examples include dabigatran), coenzyme Q-10, vitamin D1 (ergocalciferol) and vitamin D3 (cholecalciferol).

In a further aspect, suitably the active ingredient which may be present in the tablet, pellet or granule core is selected from sulfonylureas (examples include chlorpropamide, glyburide, glimeperide), thiazolidinediones (examples include rosiglitazone, pioglitazone), DPP-4 inhibitors, SGLT-2 inhibitors, aldose reductase inhibitors, phosphodiesterase-5 inhibitors, phosphodiesterase-3 inhibitor (examples include cilostazol), platelet aggregation inhibitors (examples include thienopyridines (example includes clopidigrel) prasugrel), Factor Xa inhibitors, dipyridamole, peripheral calcium channel blockers, diuretics, angiotensin converting enzyme inhibitors, angiotensin II receptor antagonists, direct thombin inhibitors (examples include dabigatran), coenzyme Q-10, vitamin D1 (ergocalciferol) and vitamin D3 (cholecalciferol).

In a further aspect suitably the active ingredient which may be present in the tablet, pellet or granule core is selected from GPR40 agonists (examples include TAK 875 and AMG 837), antiobesity drugs (examples include Qnexa (a fixed dose combination of phentermine and topiramate), Contrave (a fixed dose combination of bupriopion and naltresone) and Lorqess (lorcaserin).

In a further aspect of the invention there is provided a method of treating cardiovascular diseases comprising administering a suitable formulation of the invention to a warm-blooded animal, such as a human being, in need of such treatment.

It will be understood that the active ingredients used will depend on the disease or condition to be treated, and the skilled person will understand the uses of the active ingredients described above.

In a further aspect of the invention there is provided the use of the pharmaceutical formulation for the treatment of cardiovascular diseases, thrombotic and/or diabetic diseases.

In a further aspect of the invention there is provided the use of the pharmaceutical formulation in the manufacture of a medicament for the treatment of cardiovascular diseases, thrombotic and/or diabetic diseases.

In one embodiment of these aspects, the use is for the treatment of cardiovascular diseases. In another embodiment, the use is for the treatment of cardiovascular and thrombotic diseases. In a further embodiment, the use is for the treatment of cardiovascular and diabetic diseases.

In a further aspect of the invention there is provided a process for the manufacture of a formulation comprising spray coating a solution comprising rosuvastatin calcium and a first coating polymer in water onto a tablet, pellet or granule core.

In a further aspect of the invention, there is provided a process for the manufacture of a formulation comprising spray coating a solution comprising rosuvastatin calcium and a first coating polymer in water onto a tablet, pellet or granule core to provide a rosuvastatin calcium containing layer.

In a further aspect of the invention, there is further provided a process for the manufacture of a formulation comprising:

a) Coating a tablet, pellet or granule core with a sub-coating layer of a second coating polymer;

b) Spray coating the solution comprising rosuvastatin calcium and a first coating polymer in water onto the coated tablet, pellet or granule core to provide a rosuvastatin calcium containing layer.

In a further aspect of the invention, there is further provided a process for the manufacture of a formulation comprising:
a) Optionally coating a tablet, pellet or granule core with a sub-coating layer of a second coating polymer;
b) Spray coating the solution comprising rosuvastatin calcium and a first coating polymer in water onto the (optionally coated) tablet, pellet or granule core to provide a rosuvastatin calcium containing layer; and
c) Coating the rosuvastatin calcium containing layer with an outer coating comprising a third coating polymer.

In one embodiment of the above aspects of the invention, the tablet, pellet or granule core comprises an active ingredient which is not rosuvastatin calcium and is, in particular, selected from the lists of active ingredients described hereinbefore.

Conveniently in the above aspects and embodiments of the invention, the first coating polymer comprises HPMC and PEG, or PVA and PEG, (more particularly HPMC and PEG) as the major constituents. Further, the first coating polymer conveniently also comprises a stabilisation agent, such as calcium acetate or BHA, particularly calcium acetate.

Conveniently, the first coating polymer, second coating polymer (where used) and third coating polymer (where used) are all the same, and in particular all comprise HPMC and PEG, or PVA and PEG, more particularly all comprise HPMC and PEG. It will be understood that even where the first coating polymer, second coating polymer (where used) and third coating polymer (where used) are described herein as all the same, each layer may comprise different additional components. For example, the rosuvastatin calcium containing layer may also comprise stabilisation agents as hereinbefore described, and the outer coating may also comprise additives (in particular ferric oxide), such that it provides protection from light degradation of the rosuvastatin calcium.

In one aspect, the sub-coating layer (where used), rosuvastatin calcium containing layer and outer coating layer (where used) are all applied by spray coating techniques.

In a further aspect of the invention, there is provided a process for the manufacture of a formulation comprising:
a) Optionally coating a tablet, pellet or granule core with a sub-coating layer of an HPMC/PEG polymer (optionally comprising additional components as hereinbefore described, particularly calcium acetate or BHA, more particularly calcium acetate);
b) Spray coating a solution comprising rosuvastatin calcium and an HPMC/PEG polymer in water onto the (optionally coated) tablet, pellet or granule core to provide a rosuvastatin calcium containing layer.

In a further aspect of the invention, there is further provided a process for the manufacture of a formulation comprising:
a) Optionally coating a tablet, pellet or granule core with a sub-coating layer of an HPMC/PEG polymer (optionally comprising additional components as hereinbefore described, particularly calcium acetate or BHA, more particularly calcium acetate);
b) Spray coating a solution comprising rosuvastatin calcium and an HPMC/PEG polymer in water onto the (optionally coated) tablet, pellet or granule core to provide a rosuvastatin calcium containing layer; and
c) Coating the rosuvastatin calcium containing layer with an outer coating comprising an HPMC/PEG polymer (optionally comprising additional components, such as ferric oxide).

In one aspect of these processes above, the tablet, pellet or granule core comprises an active ingredient which is not rosuvastatin calcium. In a further aspect, this active ingredient is also not selected from any one or more of: niacin or a niacin analogue, a fibrate, metformin, a CETP inhibitor and/or aspirin. In a further aspect this active ingredient is useful for treating cardiovascular, thrombotic or diabetic diseases, although preferably is not one of the agents listed in the aspect within this paragraph above. In a further aspect, this active ingredient is selected from those listed hereinbelow:

sulfonylureas (examples include chlorpropamide, glyburide, glimeperide), thiazolidinediones (examples include rosiglitazone, pioglitazone), DPP-4 inhibitors, SGLT-2 inhibitors, aldose reductase inhibitors, phosphodiesterase-5 inhibitors, phosphodiesterase-3 inhibitor (examples include cilostazol), platelet aggregation inhibitors (examples include thienopyridines (example includes clopidigrel) prasugrel), Factor Xa inhibitors, dipyridamole, peripheral calcium channel blockers, diuretics, angiotensin converting enzyme inhibitors, angiotensin II receptor antagonists, direct thombin inhibitors (examples include dabigatran), coenzyme Q-10, vitamin D1 (ergocalciferol) and vitamin D3 (cholecalciferol), GPR40 agonists (examples include TAK 875 and AMG 837), antiobesity drugs (examples include Qnexa™ (a fixed dose combination of phentermine and topiramate), Contrave™ (a fixed dose combination of bupriopion and naltresone) and Lorqess™ (lorcaserin).

In one embodiment of all the aspects of the processes above, the rosuvastatin containing layer comprises rosuvastatin calcium and the first coating polymer in a ratio of between approximately 1:8 to 2:1

In a still further aspect of the invention is provided a product obtainable by the process as hereinbefore described. In a still further aspect of the invention is provided a product obtained by the process as hereinbefore described.

A further aspect of the invention comprises a stable solution of rosuvastatin calcium and an HPMC/PEG polymer in water.

The suitability of the formulations of the invention may be assessed by monitoring the formation of degradation products as prescribed by the ICH (International Conference on Harmonisation) Guidelines. Analysis of the degradation of the product under specific conditions for specific periods of time determines the possible shelf life and storage conditions of the product.

Further aspects of the invention comprise:
1. A pharmaceutical formulation comprising a rosuvastatin calcium containing layer spray coated onto a tablet, pellet or granule core, said rosuvastatin calcium containing layer comprising rosuvastatin calcium and a first coating polymer in a ratio of between approximately 1:8 to 2:1.
2. A pharmaceutical formulation as defined in 1, wherein the rosuvastatin calcium containing layer further comprises a stabilisation agent.
3. A pharmaceutical formulation as defined in 1 or 2 wherein tablet, pellet or granule core is coated with a sub-coating of a second coating polymer prior to spray coating with the rosuvastatin calcium containing layer.

4. A pharmaceutical formulation as defined in 3 wherein the first and second coating polymers are the same.

5. A pharmaceutical formulation as defined above wherein the rosuvastatin calcium containing layer is further coated with an outer coating of a third coating polymer.

6. A pharmaceutical formulation as defined in 5 wherein the outer coating further comprises a colourant and/or a light opacifier.

7. A pharmaceutical formulation as defined in 5 or 6 wherein the third coating polymer is the same as the second coating polymer.

8. A process for formation of the formulation defined in any one of 1 to 7, said process comprising spray coating a solution comprising rosuvastatin calcium and a first coating polymer in water onto a tablet, pellet or granule core.

EXAMPLES

The tablets in the examples described below were coated using a perforated drum coater but other pharmaceutically acceptable coating equipment may also be used.

The core tablets were capsule shaped and had the following approximate dimensions: 9.8 mm×19.3 mm with a thickness of approximately 8 mm.

Hereinbelow the term "subcoat" refers to the sub-coating layer, the term "Agent Coat" refers to the rosuvastatin calcium containing layer and the term "top coat" refers to the outercoating layer".

Example 1

TABLE 1

| Example 1 formulation | |
|---|---|
| | per tab (mg) |
| Core Tablets | 1200 |
| Opadry YS-1-10925A | 60 |
| Water | 740 |

The core tablets were coated using a mixture containing Opadry YS-1-10925A and water. Spraying was carried out at a rate of 70 g/min, for 184 minutes, with an inlet temperature of 70-72° C.

Example 2

TABLE 2

| | per tab (mg) |
|---|---|
| Core Tablets | 1200 |
| Opadry II 85F19250 | 60 |
| Water | 740 |

The core tablets were coated using a mixture containing Opadry II 85F19250 and water. Spraying was carried out at a rate of 70 g/min, for 160 minutes, with an inlet temperature of 70-73° C.

Example 3

TABLE 3

| | per tab (mg) |
|---|---|
| Subcoat | |
| As Example 1 | |
| Agent Coat | |
| Subcoated Tablets | 1293 |
| Agent | 20.8 |
| Opadry YS-1-10925A | 166.4 |
| Water | 3972.8 |
| Top Coat | |
| Agent Coated Tablets | 1484 |
| Opadry 03B94523 | 72.3 |
| Water | 891.7 |

The coated core tablets were coated using a mixture of the Agent, Opadry YS-1-10925A, and water. Spraying was carried out at a rate of 15 g/min, for 330 minutes, with an inlet temperature of 56.0-61.9° C.

After the Agent coating was complete, the tablets were coated with a top coat system consisting of Opadry 03B94523 and water. Spraying was carried out at a rate of 15 g/min, for 70 minutes, with an inlet temperature of 60.8-62.5° C.

Example 4

TABLE 4

| | per tab (mg) |
|---|---|
| Subcoat | |
| As example 1 | |
| Agent Coat | |
| Subcoated Tablets | 1293 |
| Agent | 20.8 |
| Opadry YS-1-10925A | 166.4 |
| Water | 3972.8 |
| Top Coat | |
| Agent Coated Tablets | 1480 |
| Opadry 03B94523 | 72.3 |
| Water | 891.7 |

The coated core tablets were coated using a mixture of the Agent, Opadry YS-1-10925A, and water. Spraying was carried out at a rate of 15 g/min, for 342 minutes, with an inlet temperature of 69.1-72.7° C.

After the Agent coating was complete, the tablets were coated with a top coat system consisting of Opadry 03B94523 and water. Spraying was carried out at a rate of 15 g/min, for 50 minutes, with an inlet temperature of 52.2-58.5° C.

Example 5

TABLE 5

|  | per tab (mg) |
|---|---|
| Subcoat |  |
| As example 1 |  |
| Agent Coat |  |
| Subcoated Tablets | 1293 |
| Agent | 20.8 |
| Opadry YS-1-10925A | 166.4 |
| BHA | 0.52 |
| Ethanol USP | 4.68 |
| Water | 3967.6 |
| Top Coat |  |
| Agent Coated Tablets | 1482 |
| Opadry 03B94523 | 72.3 |
| Water | 891.7 |

The coated core tablets were coated using a mixture of the Agent, Opadry YS-1-10925A, BHA-ethanol solution and water. Spraying was carried out at a rate of 15 g/min, for 340 minutes, with an inlet temperature of 58.4-61.0° C.

After the Agent coating was complete, the tablets were coated with a top coat system consisting of Opadry 03B94523 and water. Spraying was carried out at a rate of 15 g/min, for 65 minutes, with an inlet temperature of 62.0-65.1° C.

Example 6

TABLE 6

|  | per tab (mg) |
|---|---|
| Subcoat |  |
| As example 1 |  |
| Agent Coat |  |
| Subcoated Tablets | 1293 |
| Agent | 20.8 |
| Opadry YS-1-10925A | 166.4 |
| BHA | 0.52 |
| Ethanol USP | 4.68 |
| Water | 3967.6 |
| Top Coat |  |
| Agent Coated Tablets | 1481 |
| Opadry 03B94523 | 72.3 |
| Water | 891.7 |

The coated core tablets were coated using a mixture of the Agent, Opadry YS-1-10925A, BHA-ethanol solution and water. Spraying was carried out at a rate of 15 g/min, for 360 minutes, with an inlet temperature of 66.0-73.6° C.

After the Agent coating was complete, the tablets were coated with a top coat system consisting of Opadry 03B94523 and water. Spraying was carried out at a rate of 15 g/min, for 68 minutes, with an inlet temperature of 57.0-59.1° C.

Example 7

TABLE 7

|  | per tab (mg) |
|---|---|
| Subcoat |  |
| As example 1 |  |
| Agent Coat |  |
| Subcoated Tablets | 1285 |
| Agent | 20.8 |
| Opadry II 85F19250 | 166.4 |
| Water | 3972.8 |
| Top Coat |  |
| Agent Coated Tablets | 1475 |
| Opadry II 85F94317 | 72.3 |
| Water | 891.7 |

The coated core tablets were coated using a mixture of the Agent, Opadry II 85F19250, and water. Spraying was carried out at a rate of 15 g/min, for 307 minutes, with an inlet temperature of 56.5-66.1° C.

After the Agent coating was complete, the tablets were coated with a top coat system consisting of Opadry II 85F94317 and water. Spraying was carried out at a rate of 15 g/min, for 54 minutes, with an inlet temperature of 59.2-69.9° C.

Example 8

TABLE 8

|  | per tab (mg) |
|---|---|
| Subcoat |  |
| As example 2 |  |
| Agent Coat |  |
| Subcoated Tablets | 1285 |
| Agent | 20.8 |
| Opadry II 85F19250 | 166.4 |
| Water | 3972.8 |
| Top Coat |  |
| Agent Coated Tablets | 1476 |
| Opadry II 85F94317 | 72.3 |
| Water | 891.7 |

The coated core tablets were coated using a mixture of the Agent, Opadry II 85F19250, and water. Spraying was carried out at a rate of 15 g/min, for 330 minutes, with an inlet temperature of 68.0-76.8° C.

After the Agent coating was complete, the tablets were coated with a top coat system consisting of Opadry II 85F94317 and water. Spraying was carried out at a rate of 15 g/min, for 48 minutes, with an inlet temperature of 65.0-72.6° C.

Example 9

TABLE 9

|  | per tab (mg) |
|---|---|
| Subcoat |  |
| As example 2 |  |
| Agent Coat |  |
| Subcoated Tablets | 1285 |
| Agent | 20.8 |
| Opadry II 85F19250 | 166.4 |
| BHA | 0.52 |
| Ethanol USP | 4.68 |
| Water | 3967.6 |
| Top Coat |  |
| Agent Coated Tablets | 1488 |
| Opadry II 85F94317 | 72.3 |
| Water | 891.7 |

The coated core tablets were coated using a mixture of the Agent, Opadry II 85F19250, BHA-ethanol solution and water. Spraying was carried out at a rate of 15 g/min, for 290 minutes, with an inlet temperature of 54.9-65.4° C.

After the Agent coating was complete, the tablets were coated with a top coat system consisting of Opadry II 85F94317 and water. Spraying was carried out at a rate of 15 g/min, for 50 minutes, with an inlet temperature of 64.5-70.5° C.

Example 10

TABLE 10

|  | per tab (mg) |
|---|---|
| Subcoat |  |
| As example 2 |  |
| Agent Coat |  |
| Subcoated Tablets | 1285 |
| Agent | 20.8 |
| Opadry II 85F19250 | 166.4 |
| BHA | 0.52 |
| Ethanol USP | 4.68 |
| Water | 3967.6 |
| Top Coat |  |
| Agent Coated Tablets | 1461 |
| Opadry II 85F94317 | 72.3 |
| Water | 891.7 |

The coated core tablets were coated using a mixture of the Agent, Opadry II 85F19250, BHA-ethanol solution and water. Spraying was carried out at a rate of 15 g/min, for 330 minutes, with an inlet temperature of 67.8-75.7° C.

After the Agent coating was complete, the tablets were coated with a top coat system consisting of Opadry II 85F94317 and water. Spraying was carried out at a rate of 15 g/min, for 62 minutes, with an inlet temperature of 66.0-70.3° C.

Example 11

TABLE 11

|  | per tab (mg) |
|---|---|
| Subcoat |  |
| Core Tablets | 1228 |
| Opadry YS-1-10925A | 86.4 |
| Water | 1065.6 |
| Agent Coat |  |
| Subcoated Tablets | 1310 |
| Agent | 10.4 |
| Opadry YS-1-10925A | 83.2 |
| Water | 1986.4 |
| Top Coat |  |
| No Top Coat |  |

The core tablets were coated using a mixture containing Opadry YS-1-10925A and water. Spraying was carried out at a rate of 15 g/min, for 119 minutes, with an inlet temperature of 65.9-68.9° C. Then the coated core tablets were coated using a mixture of the Agent, Opadry YS-1-10925A, and water. Spraying was carried out at a rate of 15 g/min, for 180 minutes, with an inlet temperature of 61.5-68.0° C.

Example 12

TABLE 12

|  | per tab (mg) |
|---|---|
| Subcoat |  |
| Core Tablets | 1228 |
| Opadry YS-1-10925A | 111 |
| Water | 1369 |
| Agent Coat |  |
| Subcoated Tablets | 1342 |
| Agent | 10.4 |
| Opadry YS-1-10925A | 83.2 |
| Water | 1986.4 |
| Top Coat |  |
| No Top Coat |  |

The core tablets were coated using a mixture containing Opadry YS-1-10925A and water. Spraying was carried out at a rate of 15 g/min, for 140 minutes, with an inlet temperature of 59.4-65.0° C. Then the coated core tablets were coated using a mixture of the Agent, Opadry YS-1-10925A, and water. Spraying was carried out at a rate of 15 g/min, for 175 minutes, with an inlet temperature of 62.0-68.1° C.

Example 13

TABLE 13

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 20.8 |
| Water | 4118.4 |
| Top Coat | |
| Agent Coated Tablets | 1325 |
| Opadry 03B94523 | 26.7 |
| Water | 1041.3 |

The coated core tablets were coated using a mixture of the Agent, Opadry YS-1-10925A, and water. Spraying was carried out at a rate of 15 g/min, for 311 minutes, with an inlet temperature of 62.4-70.5° C. After the Agent coating was complete, the tablets were coated with a top coat system consisting of Opadry 03B94523 and water. Spraying was carried out at a rate of 15 g/min, for 60 minutes, with an inlet temperature of 67.0-72.3° C.

Example 14

TABLE 14

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 83.2 |
| Water | 4056 |
| Top Coat | |
| Agent Coated Tablets | 1385 |
| Opadry 03B94523 | 26.7 |
| Water | 1041.3 |

The coated core tablets were coated using a mixture of the Agent, Opadry YS-1-10925A, and water. Spraying was carried out at a rate of 15 g/min, for 306 minutes, with an inlet temperature of 63.3-73.1° C. After the Agent coating was complete, the tablets were coated with a top coat system consisting of Opadry 03B94523 and water. Spraying was carried out at a rate of 15 g/min, for 60 minutes, with an inlet temperature of 54.5-70.8° C.

Example 15

TABLE 15

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 10.4 |
| Water | 4128.8 |
| Top Coat | |
| Agent Coated Tablets | 1326 |
| Opadry 03B94523 | 25 |
| Water | 975 |

The coated core tablets were coated using a mixture of the Agent, Opadry YS-1-10925A, and water. Spraying was carried out at a rate of 15 g/min, for 435 minutes, with an inlet temperature of 66.0-71.7° C. After the Agent coating was complete, the tablets were coated with a top coat system consisting of Opadry 03B94523 and water. Spraying was carried out at a rate of 15 g/min, for 90 minutes, with an inlet temperature of 64.5-68.8° C.

Example 16

TABLE 16

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 20.8 |
| Water | 4118.4 |
| Top Coat | |
| Agent Coated Tablets | 1335 |
| Opadry 03B94523 | 25 |
| Water | 975 |

The coated core tablets were coated using a mixture of the Agent, Opadry YS-1-10925A, and water. Spraying was carried out at a rate of 15 g/min, for 435 minutes, with an inlet temperature of 66.0-74.4° C. After the Agent coating was complete, the tablets were coated with a top coat system consisting of Opadry 03B94523 and water. Spraying was carried out at a rate of 15 g/min, for 85 minutes, with an inlet temperature of 66.5-69.7° C.

Example 17

TABLE 17

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 31.2 |
| Water | 4108 |
| Top Coat | |
| Agent Coated Tablets | 1349 |
| Opadry 03B94523 | 25 |
| Water | 975 |

The coated core tablets were coated using a mixture of the Agent, Opadry YS-1-10925A, and water. Spraying was carried out at a rate of 15 g/min, for 438 minutes, with an inlet temperature of 66.7-71.1° C. After the Agent coating was complete, the tablets were coated with a top coat system consisting of Opadry 03B94523 and water. Spraying was carried out at a rate of 15 g/min, for 95 minutes, with an inlet temperature of 66.0-70.0° C.

Example 18

TABLE 18

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 20.8 |
| Calcium Acetate | 6.6 |
| Water | 4118.4 |
| Top Coat | |
| Agent Coated Tablets | 1335 |
| Opadry 03B94523 | 25 |
| Water | 975 |

The coated core tablets were coated using a mixture of the Agent, calcium acetate, Opadry YS-1-10925A, and water. Spraying was carried out at a rate of 15 g/min, for 390 minutes, with an inlet temperature of 66.4-68.0° C. After the Agent coating was complete, the tablets were coated with a top coat system consisting of Opadry 03B94523 and water. Spraying was carried out at a rate of 15 g/min, for 70 minutes, with an inlet temperature of 67.5-73.7° C.

Example 19

|  | per tab (mg) |
|---|---|
| Subcoat | |
| As example 1 | |
| Agent Coat | |
| Subcoated Tablets | 1293 |
| Agent | 20.8 |
| Opadry YS-1-10925A | 20.8 |
| Sodium Hydroxide | 0.8 |
| Water | 4117.6 |
| Top Coat | |
| Agent Coated Tablets | 1337 |
| Opadry 03B94523 | 25 |
| Water | 975 |

The coated core tablets were coated using a mixture of the Agent, sodium hydroxide solution, Opadry YS-1-10925A, and water. Spraying was carried out at a rate of 15 g/min, for 390 minutes, with an inlet temperature of 67.0-68.5° C. After the Agent coating was complete, the tablets were coated with a top coat system consisting of Opadry 03B94523 and water. Spraying was carried out at a rate of 15 g/min, for 70 minutes, with an inlet temperature of 69.0-75.0° C.

Moisture Values after Coating and Heating at 50° C. for 24 h in % w/w

| Example | Subcoat | Agent Coating | Top Coat |
|---|---|---|---|
| 1 | 1.00 | N/A | N/A |
| 2 | 1.46 | N/A | N/A |
| 3 | See Example 1 | 2.17 | 1.74 |
| 4 | See Example 1 | 1.41 | 1.37 |
| 5 | See Example 1 | 2.34 | 1.89 |
| 6 | See Example 1 | 1.38 | 1.28 |
| 7 | See Example 2 | 3.25 | 3.11 |
| 8 | See Example 2 | 2.07 | 1.96 |
| 9 | See Example 2 | 3.60 | 2.92 |
| 10 | See Example 2 | 1.98 | 1.98 |
| 11 | 0.79 | 1.26 | No Top Coat |
| 12 | 0.95 | 1.20 | No Top Coat |
| 13 | See Example 1 | 0.78 | 0.81 |
| 14 | See Example 1 | 0.76 | 0.89 |
| 15 | See Example 1 | 0.94 | 0.90 |
| 16 | See Example 1 | 0.86 | 0.83 |
| 17 | See Example 1 | 0.79 | 0.76 |
| 18 | See Example 1 | 0.81 | 0.97 |
| 19 | See Example 1 | 1.34 | 1.26 |

Lactone Formation (% w/w)

The stability of the formulations of the invention is illustrated in FIG. 1 by the following stability information.

|  | Example 3 (labelled as 10 below) |  | Example 13 (labelled as 22 below) |  | Example 18 (labelled as 27 below) | Example 19 (labelled as 28 below) |
|---|---|---|---|---|---|---|
| 0 month | 0.273 | 0 month | 0.060 | 0 month | 0.041 | 0.055 |
| 1 month | 0.471 | 1 month | 0.120 | 1 month | 0.058 | 0.089 |
| 3 month | 0.848 | 8 month | 0.235 | 7 month | 0.071 | 0.198 |

The invention claimed is:
1. A coating solution comprising water, rosuvastatin calcium, calcium acetate and a polymer mixture of HPMC and PEG, wherein the weight ratio of rosuvastatin calcium to the polymer mixture is approximately 1:8 to 2:1.

* * * * *